United States Patent [19]

Böhner et al.

[11] Patent Number: 5,217,524
[45] Date of Patent: Jun. 8, 1993

[54] 1,5-DIPHENYL-1,2,4-TRIAZOLE-3-CARBOXYLIC ACID DERIVATIVES FOR THE PROTECTION OF CULTIVATED PLANTS FROM THE PHYTOTOXIC ACTION OF HERBICIDES

[75] Inventors: Beat Böhner, Binningen; Hans Moser, Magden, both of Switzerland

[73] Assignee: Ciba-Geigy Corporation, Ardsley, N.Y.

[21] Appl. No.: 764,756

[22] Filed: Sep. 24, 1991

Related U.S. Application Data

[62] Division of Ser. No. 07/248,077, Sep. 23, 1988, Pat. No. 5,077,413.

[30] Foreign Application Priority Data

Oct. 2, 1987 [CH] Switzerland .......................... 3858/87

[51] Int. Cl.$^5$ ..................... A01N 43/40; A01N 43/653
[52] U.S. Cl. .................................................. 504/106
[58] Field of Search .............................. 71/92, 94, 106

[56] References Cited

FOREIGN PATENT DOCUMENTS 189300 7/1986 European Pat. Off. .

Primary Examiner—Richard L. Raymond
Assistant Examiner—Brian G. Bembenick
Attorney, Agent, or Firm—Edward McC. Roberts

[57] ABSTRACT 1,5-Diphenyl-1,2,4-triazole-3-carboxylic acid derivatives of formula

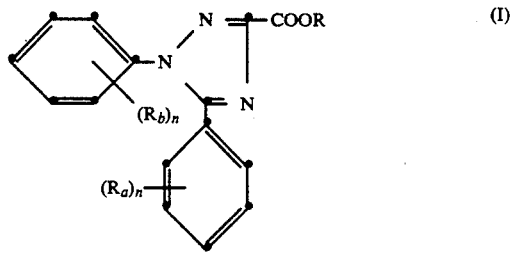

wherein each of $R_a$ and $R_b$, independently of the other, is halogen, $C_1$-$C_5$alkyl, $C_1$-$C_5$haloalkyl, $C_2$-$C_5$alkenyl, $C_2$-$C_5$alkynyl or cyano, n is zero or a number from 1 to 3 and OR is hydroxy, a phytophysiologically tolerable metal or ammonium salt radical, or an ester radical defined in the description, are capable of specifically antagonising the phytotoxic action of herbicides.

1,5-Diphenyl-1,2,4-triazole-3-carboxylic acid derivatives of formula I and the preparation thereof, compositions containing these components as selective herbicides and the use of these two active ingredient components for controlling weeds in crops of useful plants are described.

6 Claims, No Drawings

1,5-DIPHENYL-1,2,4-TRIAZOLE-3-CARBOXYLIC ACID DERIVATIVES FOR THE PROTECTION OF CULTIVATED PLANTS FROM THE PHYTOTOXIC ACTION OF HERBICIDES

This is a divisional of U.S. application Ser. No. 248,077, filed Sep. 23, 1988, now U.S. Pat. No. 5,077,413, issued Dec. 31, 1991.

The present invention relates to 1,5-diphenyl-1,2,4-triazole-3-carboxylic acid derivatives that are suitable for protecting cultivated plants against damaging effects of herbicidally active phenoxyalkanecarboxylic acid esters. The invention also relates to herbicidal compositions that contain a combination of herbicide and protecting 1,5-diphenyl-1,2,4-triazolecarboxylic acid or a derivative thereof.

Depending on factors such as, for example, dosage of the herbicide and method of application, type of cultivated plant, nature of the soil and climatic conditions, such as, for example, duration of exposure to light, temperature and rainfall, the cultivated plants may suffer considerable damage when herbicides such as, for example, chloroacetanilides, N-benzoyl-N-phenylalanines and phenoxyalkanecarboxylic acid herbicides such as, for example, phenoxyphenoxy- and pyridylphenoxy-propionic acid derivatives are used. Severe damage may occur especially when, for a succession of fruit, cultivated plants that have no resistance or only insufficient resistance to the herbicides are grown after cultivated plants that are resistant to those herbicides.

Surprisingly, it has now been found that it is possible to achieve protection of cultivated plants against damage caused by the above-mentioned herbicides, by treating the cultivated plants, parts of those plants or soils in which the cultivated plants are to be grown, with a safener selected from the group consisting of 1,5-diphenyl-1,2,4-triazole-3-carboxylic acid derivatives. These derivatives do not affect the herbicidal action against weeds and weed grasses.

1,5-Diphenyl-1,2,4-triazole-3-carboxylic acid derivatives that are suitable for protecting cultivated plants from the damaging effects of herbicidally active phenoxyphenoxy-, benzoxazolyloxyphenoxy-, benzothiazolyloxyphenoxy-, quinoxalyloxyphenoxy- and pyridyloxyphenoxy-propionic acid derivatives correspond to formula I

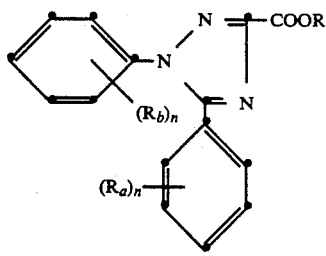

wherein each of $R_a$ and $R_b$, independently of the other, is halogen, $C_1$–$C_5$alkyl, $C_1$–$C_5$haloalkyl, $C_2$–$C_5$alkenyl, $C_2$–$C_5$alkynyl, $C_1$–$C_5$alkoxy, $C_1$–$C_5$haloalkoxy, nitro or cyano, n is zero or a number from 1 to 3 and R is hydrogen, a phytophysiologically tolerable metal or ammonium cation, $C_1$–$C_8$alkyl or $C_3$–$C_{12}$cycloalkyl each of which is unsubstituted or is mono- or poly-substituted by $C_1$–$C_4$alkoxy, $C_1$–$C_4$alkylthio, mono- or di-$C_1$–$C_4$alkylamino, amino or by $C_1$–$C_4$alkoxycarbonyl; $C_3$–$C_6$alkenyl or $C_3$–$C_{12}$cycloalkenyl each of which is unsubstituted or is mono- or poly-substituted by halogen; $C_3$–$C_6$alkynyl; phenyl or benzyl each of which is unsubstituted or is mono- or poly-substituted by halogen, nitro, $C_1$–$C_4$alkyl, $C_1$–$C_4$alkoxy, $C_1$–$C_4$alkylthio, $C_1$–$C_4$haloalkyl, $C_1$–$C_4$haloalkoxy or by cyano.

Some of these compounds are novel and some are known. The novel compounds are those which are halogenated in at least one of the phenyl nuclei, that is to say compounds of formula I with the proviso that at least one of the radicals $R_a$ and $R_b$ is chlorine or fluorine.

Phytophysiologically tolerable metal and ammonium cations are understood as being cations of salts that are customary in herbicides, such as alkali metal, alkaline earth metal, iron, copper or manganese cations, or ammonium, alkylammonium, hydroxyalkylammonium or alkoxyalkylammonium cations.

Alkyl radicals are understood as being radicals containing the indicated number of carbon atoms. These radicals may be straight-chain or branched. The most common radicals are, for example, methyl, ethyl, n-propyl, isopropyl, n-butyl, isobutyl, sec.-butyl, tert.-butyl, n-pentyl, isopentyl, n-hexyl and n-octyl. The alkenyl and alkynyl radicals may also be straight-chain chain or branched and contain from 3 to 6 carbon atoms. The most common radicals are, for example, allyl, methallyl, butenyl, butadienyl, propynyl, methylpropynyl, 1-butynyl and 2-butynyl. Cycloalkyl or cycloalkenyl radicals preferably have from 3 to 12 carbon atoms, and they may also be benzo-fused. Examples of typical representatives are cyclopropyl, cyclopentyl, cyclohexyl, cyclohexenyl, indanyl, tetrahydronaphthalinyl and decalinyl. Halogen is understood as being fluorine, chlorine, bromine or iodine, especially fluorine and chlorine. Haloalkyl and haloalkenyl radicals may be mono- or poly-substituted by halogen.

The 1,5-diphenyl-1,2,4-triazolecarboxylic acid derivatives of formula I have, to an outstanding degree, the ability to protect cultivated plants against the damaging effect of herbicides such as, for example, the following chloroacetanilides: 2-chloro-2',6'-diethyl-N-(2"-n-propoxyethyl)acetanilide ("propalochlor"), 2-chloro-6'-ethyl-N-(2"-methoxy-1"-methylethyl)acet-o-toluidide ("metolachlor"), 2-chloro-2',6'-diethyl-N-(n-butoxymethyl)acetanilide ("butachlor"), 2-chloro-6'-ethyl-N-(ethoxymethyl)acet-o-toluidide ("acetochlor"), 2-chloro-6'-ethyl-N-(2"-propoxy-1"-methylethyl)acet-o-toluidide, 2-chloro-2',6'-dimethyl-N-(2"-methoxy-1"-methylethyl)acetanilide, 2-chloro-2',6'-dimethyl-N-(2"-methoxyethyl)acetanilide ("dimethachlor"), 2-chloro-2',6'-ethyl-N-(pyrazol-1-ylmethyl)acet-o-toluidide, 2-chloro-6'-ethyl-N-(3",5"-dimethylpyrazol-1-ylmethyl)-acet-o-toluidide, 2-chloro-6'-ethyl-N-(2"-n-butoxy-1"-methylethyl)acet-o-toluidide ("metazolachlor") and 2-chloro-2'-trimethylsilyl-N-(butoxymethyl)acetanilide.

The 1,5-diphenyl-1,2,4-triazole-3-carboxylic acid derivatives of formula I also protect cultivated plants from the damaging effect of herbicidally active N-benzoyl-N-phenyl-alanine derivatives of formula XII

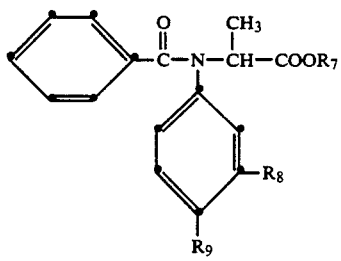

wherein $R_7$ is hydrogen or $C_1$-$C_4$alkyl and each of $R_8$ and $R_9$, independently of the other, is chlorine or fluorine, and the enantiomers thereof, especially N-benzoyl-N-(3,4-dichlorophenyl)-alanine ethyl ester and N-benzoyl-N-(3-chloro-4-fluorophenyl)-alanine methyl ester.

The 1,5-diphenyl-1,2,4-triazole-3-carboxylic acid derivatives of formula I protect the cultivated plants especially from herbicidally active 2-[4-(phenoxy, pyridin-2-yloxy, benzoxazol-2-yloxy, benzothiazol-2-yloxy or quinoxalin-2-yloxy)-phenoxy]-propionic acid esters of formula XI

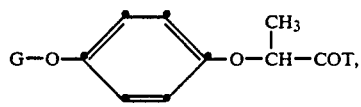

wherein G is

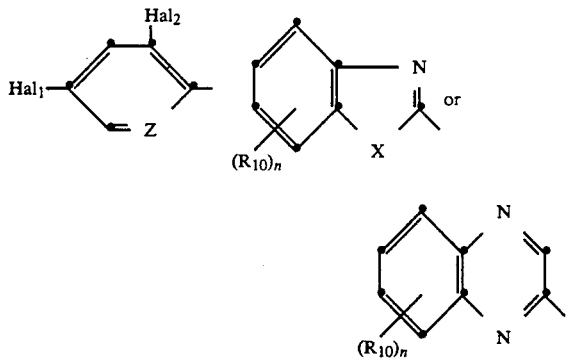

wherein $Hal_1$ is fluorine, chlorine, bromine, iodine or trifluoromethyl, $Hal_2$ is hydrogen, fluorine, chlorine, bromine or trifluoromethyl, Z is nitrogen or methine (—CH=), X is an oxygen or sulfur atom, $R_{10}$ is halogen, trifluoromethyl, nitro, cyano, $C_1$-$C_4$alkyl or $C_1$-$C_4$alkoxy and n is 0, 1, 2 or 3.

In the compounds of formula XI, halogen is fluorine, chlorine, bromine or iodine, preferably fluorine, chlorine or bromine.

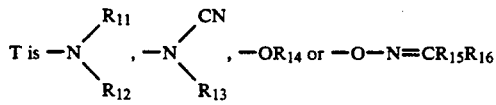

wherein each of $R_{11}$ and $R_{12}$, independently of the other, is hydrogen, $C_1$-$C_8$alkoxy, $C_1$-$C_8$alkyl, phenyl or benzyl, $R_{11}$ and $R_{12}$ together with the nitrogen atom carrying them are a 5- or 6-membered saturated nitrogen heterocycle that may be interrupted by an oxygen or sulfur atom, $R_{13}$ is $C_1$-$C_4$alkyl, $C_3$-$C_4$alkenyl, $C_3$-$C_4$alkynyl or $C_2$-$C_4$alkoxyalkyl, $R_{14}$ is hydrogen or the equivalent of an alkali metal ion, alkaline earth metal ion, copper ion or iron ion; a quaternary $C_1$-$C_4$-alkylammonium or $C_1$-$C_4$hydroxyalkylammonium radical; a $C_1$-$C_9$alkyl radical that is unsubstituted or is mono- or poly-substituted by amino, halogen, hydroxy, cyano, nitro, phenyl, $C_1$-$C_4$alkoxy, polyethoxy containing from 2 to 6 ethylene oxide units, —COOR, —COSR, —CONH$_2$, —CON($C_1$-$C_4$alkoxy)-$C_1$-$C_4$alkyl, —CO—N-di—$C_1$-$C_4$alkyl, —CONH-$C_1$-$C_4$alkyl, —N($C_1$-$C_4$alkoxy)-$C_1$-$C_4$alkyl or by di-$C_1$-$C_4$alkylamino; a $C_3$-$C_9$alkenyl radical that is unsubstituted or is substituted by halogen or by $C_1$-$C_4$alkoxy; a $C_3$-$C_9$alkynyl radical that is unsubstituted or is substituted by halogen or by $C_1$-$C_4$alkoxy; $C_3$-$C_9$cycloalkyl; or phenyl that is unsubstituted or is substituted by cyano, $C_1$-$C_4$alkyl, $C_1$-$C_4$alkoxy, acetyl, —COOR$_{17}$, —COSR$_{17}$, —CONH$_2$, —CON($C_1$-$C_4$alkoxy)-$C_1$-$C_4$alkyl, —CO—N-di-$C_1$-$C_4$alkyl or by —CONH-$C_1$-$C_4$alkyl; each of $R_{15}$ and $R_{16}$, independently of the other, is $C_1$-$C_4$alkyl or $R_{15}$ and $R_{16}$ together form a 3- to 6-membered alkylene chain, and $R_{17}$ is hydrogen, $C_1$-$C_6$alkyl, $C_1$-$C_6$haloalkyl, $C_2$-$C_6$alkoxyalkyl, $C_3$-$C_6$alkenyl, $C_3$-$C_6$haloalkenyl, $C_3$-$C_6$alkynyl or $C_3$-$C_6$-haloalkynyl.

In the compounds of formula I, halogen, as an independent substituent or as part of another substituent, such as haloalkyl, haloalkoxy, haloalkenyl or haloalkynyl, means fluorine, chlorine, bromine or iodine, among which fluorine and chlorine are preferred.

Depending on the number of carbon atoms present, alkyl is methyl, ethyl, n-propyl, isopropyl and the isomers of butyl, pentyl, hexyl, heptyl or octyl. The alkyl groups present in the radicals alkoxy, alkoxyalkyl, haloalkyl or haloalkoxy have the same meaning. Alkyl groups having a small number of carbon atoms are preferred in each case.

Preferred haloalkyl radicals, or haloalkyl moieties in haloalkoxy radicals, are: fluoromethyl, difluoromethyl, trifluoromethyl, chloromethyl, trichloromethyl, 2-fluoroethyl, 2,2,2-trifluoroethyl, 1,1,2,2-tetra-fluoroethyl, perfluoroethyl, 2-chloroethyl, 2,2,2-trichloroethyl, 2-bromoethyl and 1,1,2,3,3,3-hexafluoropropyl.

Cycloalkyl denotes mono- and bi-cyclic saturated hydrocarbon ring systems such as cyclopropyl, cyclobutyl, cyclopentyl, cyclohexyl, cycloheptyl, cyclooctyl, cyclononyl, bicyclo[4.3.0]nonyl, bicyclo[5.2.0]nonyl or bicyclo[2.2.2]octyl.

Especially worthy of mention is the protective action of triazole derivatives of formula I against those herbicides of formula XI in which T represents the groups —O—$R_{14}$ or —O—N=$CR_{15}R_{16}$, wherein $R_{14}$ is hydrogen, $C_1$-$C_4$alkyl, $C_3$-$C_4$alkynyl, or $C_1$-$C_4$alkyl that is substituted by $C_1$-$C_4$alkoxycarbonyl or by di-$C_1$-$C_4$-alkylamino, and each of $R_{15}$ and $R_{16}$, independently of the other, is $C_1$-$C_4$alkyl or $R_{15}$ and $R_{16}$ together form a $C_4$-$C_7$alkylene chain.

Individual meanings of T that should be given special prominence are methoxy, ethoxy, propoxy, isopropoxy, butoxy, dimethylaminoethoxy, propargyloxy, 1-cyano-1-methylethoxy, methoxycarbonylmethylthio, 1-ethoxycarbonylethoxy, butoxycarbonylmethoxy, —O—N=C(CH$_3$)$_2$, —O—N=C(CH$_3$)C$_2$H$_5$ or —O—N=C(CH$_2$)$_5$, and of G

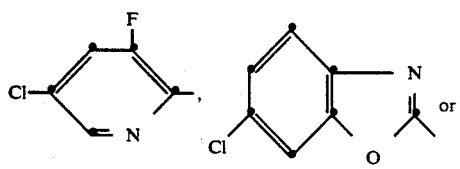

Preferred individual compounds of formula XI are:

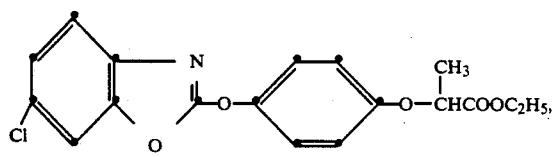

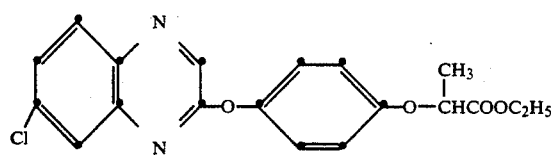

and the 2-pyridyloxyphenoxypropionic acid derivatives of the attached Table 1.

TABLE 1

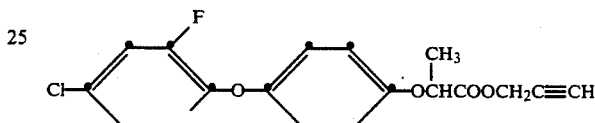

(XI)

| No. | T | physical constant |
|---|---|---|
| 1.1 | —OCH$_3$ | m.p. 63-64° C. |
| 1.2 | —OC$_4$H$_9$-n | $n_D^{35}$ = 1.5275 |
| 1.3 | —O—N=C(CH$_3$)$_2$ | $n_D^{35}$ = 1.5488 |
| 1.4 | —OC$_2$H$_5$ | $n_D^{35}$ = 1.5358 |
| 1.5 | —O—CH$_2$—CH$_2$—N(CH$_3$)$_2$ | $n_D^{35}$ = 1.5334 |
| 1.6 | —O—CH$_2$—C≡CH | $n_D^{35}$ = 1.5492 |
| 1.7 | —O—C—CN<br>   CH$_3$  CH$_3$ | $n_D^{35}$ = 1.5330 |
| 1.8 | —S—CH$_2$—COOCH$_3$ | $n_D^{35}$ = 1.5607 |
| 1.9 | —O—CH—COOC$_2$H$_5$<br>       CH$_3$ | $n_D^{35}$ = 1.5227 |
| 1.10 | —O—CH$_2$—COOC$_4$H$_9$-n | $n_D^{35}$ = 1.5223 |
| 1.11 | —OC$_3$H$_7$-n | $n_D^{35}$ = 1.5319 |
| 1.12 | —OC$_3$H$_7$-i | $n_D^{35}$ = 1.5284 |
| 1.13 | —O—N=C—C$_2$H$_5$<br>         CH$_3$ | $n_D^{35}$ = 1.5340 |
| 1.14 | —O—N=C (cyclohexylidene) | $n_D^{35}$ = 1.5360 |
| 1.15 | —OCH$_3$ (2R) | $n_D^{35}$ = 1.5359 |

TABLE 1-continued

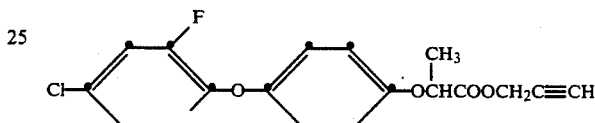

(XI)

| No. | T | physical constant |
|---|---|---|
| 1.16 | —OH | m.p. 95-97° C. |
| 1.17 | —S—CH$_2$—COOCH$_3$ (2R) | $n_D^{35}$ = 1.5623 |
| 1.18 | —O—CH—COOC$_2$H$_5$ (2R,S)<br>       CH$_3$ | $n_D^{35}$ = 1.5223 |
| 1.19 | —O—CH$_2$—C≡CH (2R) | m.p. 55-56° C. |
| 1.20 | —NH—OCH$_3$ | m.p. 103-105° C. |

Special prominence is to be given to the individual compound 1.6

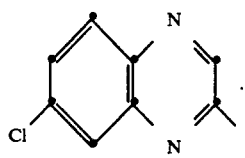

or its 2R enantiomer (compound 1.19).

Owing to the optically active carbon atom in the propionic acid group, these compounds may occur both in the R- and in the S-configuration. Unless specified, the racemic mixtures are meant herein. Preferred herbicides of formula I are in the 2R-configuration.

Cultivated plants that can be protected by 1,5-diphenyl-1,2,4-triazole-3-carboxylic acids and derivatives of formula I against harmful effects of the above-mentioned herbicides are especially those that are important in the food and textile sectors, for example sugar cane and especially cultivated sorghum, maize, rice and other varieties of cereal (wheat, rye, barley, oats).

Some of the 1,5-diphenyl-1,2,4-triazole-3-carboxylic acid derivatives of formula I are known compounds and some are novel compounds. Compounds that are novel and that are especially effective as antidotes to the above-mentioned herbicides are those in which at least one of the substituents $R_a$ and $R_b$ is chlorine or fluorine, especially those corresponding to formula Ia

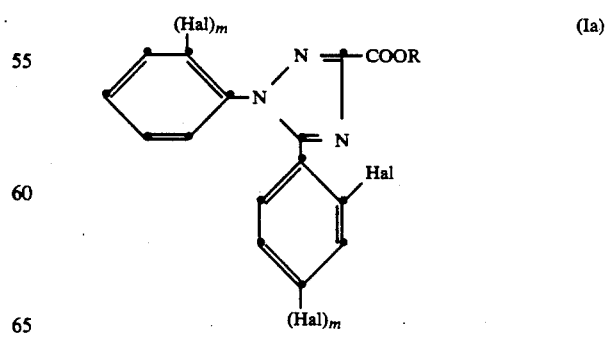

(Ia)

wherein Hal is a halogen atom, m is zero or 1 and R is as defined for formula I. Compounds of formula Ib

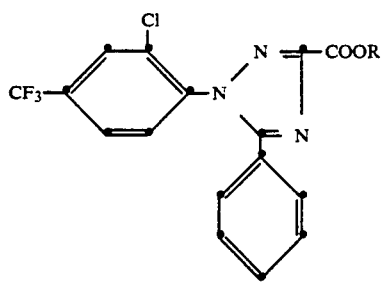

(Ib)

wherein R is as defined for formula I, but is especially methyl or ethyl, have also been found to be very good antidotes.

The 1,5-diphenyl-1,2,4-triazole-3-carboxylic acids and derivatives of formula I

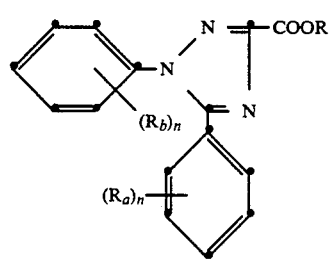

(I)

can be prepared by various methods of synthesis that are known per se.

Their preparation is described, for example, in the following literature in which 1,5-diphenyl-1,2,4-triazole-3-carboxylic acid derivatives have been mentioned as intermediates or end products:
DE-PS 1 123 331,
US-PS 4 492 597,
EP-A 200 956,
J. Chem. Soc. 1962 575–583,
J. Chem. Soc. 1985 103–105,
J. Chem. Soc. 79 1955–56 (1957),
Chem. and Ind. 1960 1086,
Synthesis 1986 772,
J. Am. Chem. Soc. 79 (1957) 1955,
J. Chem. Soc. 87 (1905) 1859,
Chem. Ber. 50 (1917) 1482.

We have prepared the 1,5-diphenyl-1,2,4-triazole-3-carboxylic acid derivatives according to the methods of synthesis shown in the following reaction schemes.

According to a first process of the invention, a phenylhydrazine of formula VII is condensed with a thiooxamide acid alkyl ester, with hydrogen sulfide being split off. The resulting condensation product of formula IX is then cyclised by heating with an orthobenzoic acid trialkyl ester of formula X, e.g. the triethyl ester, to form the 1,5-diphenyl-1,2,4-triazole-3-carboxylic acid derivative of formula I.

Scheme 1:

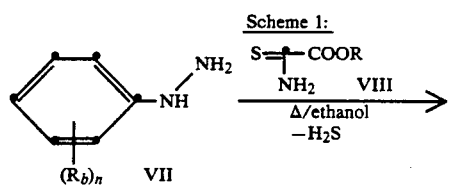

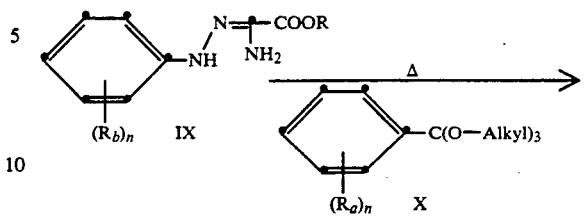

According to a second process, analogous to J. Chem. Soc. 87 (1905) 1859, an aniline is reacted with sodium nitrite and hydrochloric acid, and a 2-chloroacetoacetic acid alkyl ester is added to the resulting diazo compound. The condensation product is treated with ammonia and cyclised with a benzoyl chloride to give the 1,5-diphenyl-1,2,4-triazole-3-carboxylic acid derivative.

Scheme 2:

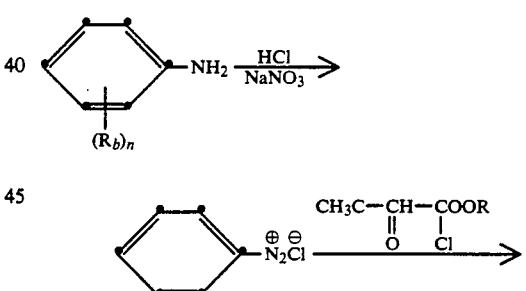

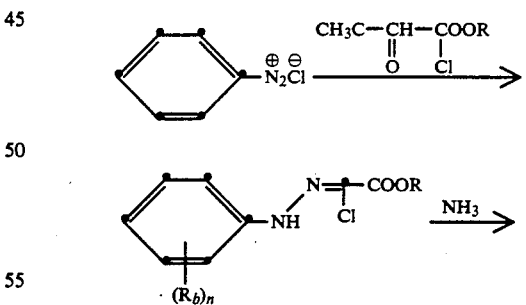

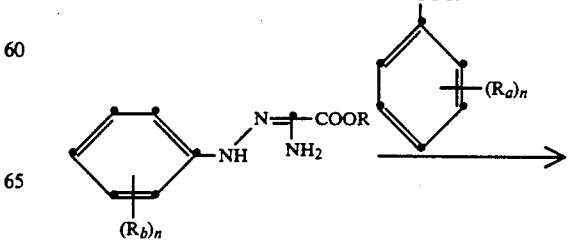

-continued
Scheme 2:

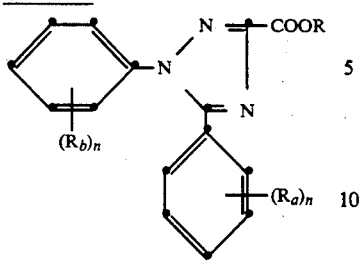

5

10

According to a third process, analogous to DE-PS 1 123 331, first an aniline is diazotised using sodium nitrite and hydrochloric acid and then a benzoylaminomalonic acid dialkyl ester is added. The condensation product is then cyclised under conditions that remove the elements of water, for example with sodium methoxide in methanol here, to give the 1,5-diphenyl-1,2,4-triazole-3-carboxylic acid derivative.

Scheme 3:

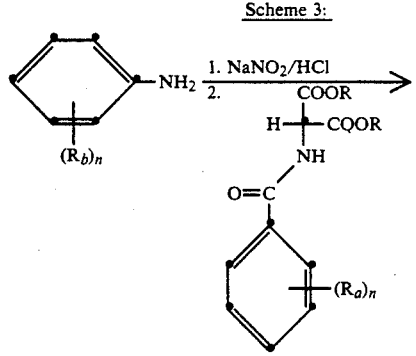

-continued
Scheme 3:

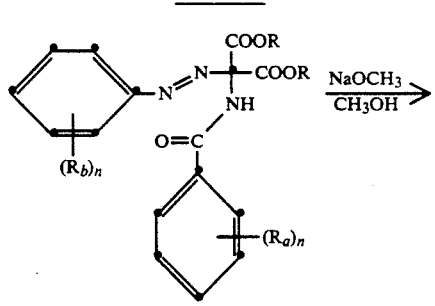

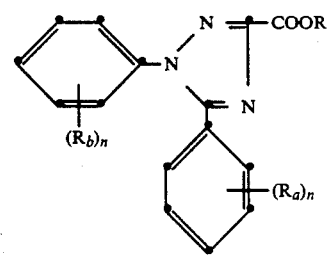

A general process for the preparation of 1,5-diphenyl-1,2,4-triazole-3-carboxylic acid derivatives of formula I, which is partly described in J. Am. Chem. Soc. 79 (1957) 1955, can be represented by the following Scheme 4:

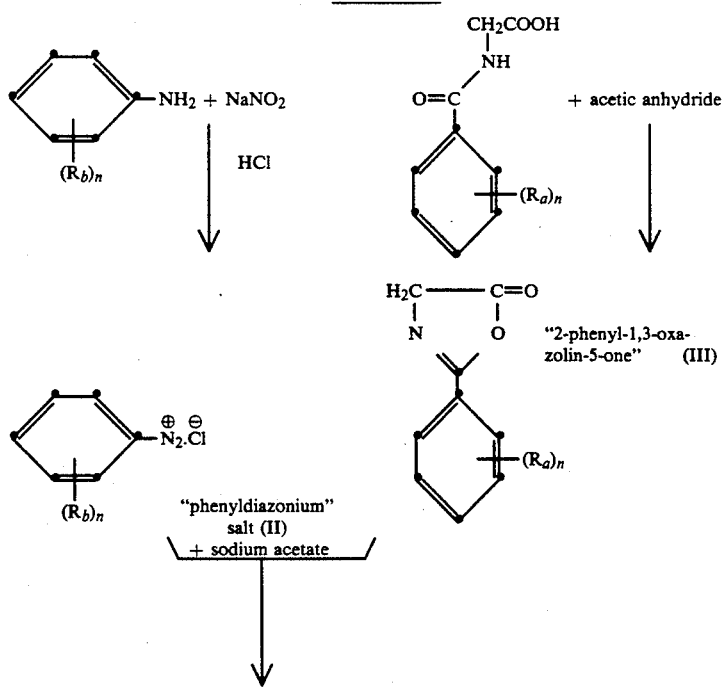

Scheme 4:

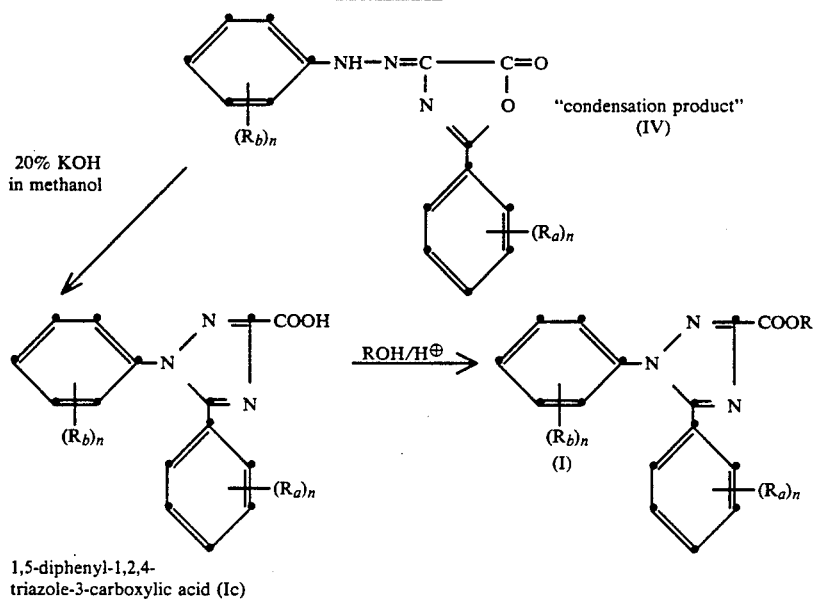

1,5-diphenyl-1,2,4-
triazole-3-carboxylic acid (Ic)

The process of the invention for the preparation of the 1,5-diphenyl-1,2,4-triazole-3-carboxylic acid derivatives of formula I comprises condensing a phenyldiazonium salt of formula II

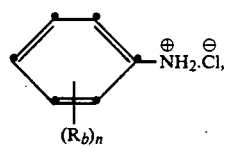  (II)

wherein n and $R_b$ are as defined for formula 2-phenyl-1,3-oxazolin-5-one of formula III

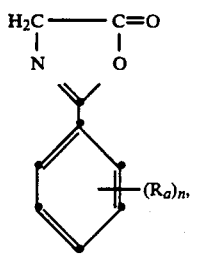  (III)

wherein n and $R_a$ are as defined for formula I, in the presence of sodium acetate, and cyclising the resulting condensation product of formula IV

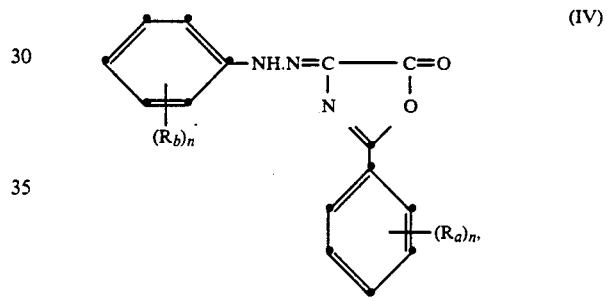  (IV)

wherein n, $R_a$ and $R_b$ are as defined for formula I, by heating, and, if desired, esterifying the resulting 1,5-diphenyl-1,2,4-triazole-3-carboxylic acid of formula Ic

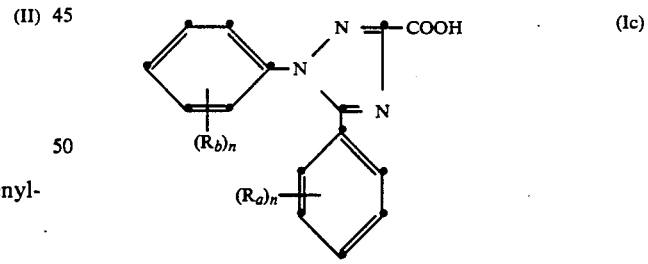  (Ic)

with an alcohol of formula V

HO—R  (V)

wherein R is as defined for formula I.

These reaction steps and variations thereof are described in the literature, for example in the reference work mentioned above. The starting materials are known.

Suitable solvents for the condensation are corresponding alcohols, such as methanol or ethanol; acetone and higher-boiling ketones, such as methyl ethyl ketone; but also higher-boiling ethers such as dipropyl ether, dioxane or tetrahydrofuran; and aromatic hydrocarbons, such as benzene, toluene or xylene.

The reaction temperatures are in the range of from 0° C. to 200° C. Preferably, however, the reaction will be carried out at from 0° C. to the boiling point of the reaction mixture.

The following Examples describe the preparation of 1,5-diphenyl-1,2,4-triazole-3-carboxylic acid derivatives of the invention. Temperatures are given in degrees Celsius.

Examples of other compounds that have a protective action against herbicides and that are to be used according to the invention are listed thereafter in Table 2.

EXAMPLE 1

Preparation of 1-(2-chloro-4-trifluoromethylphenyl)-5-phenyl-1,2,4-triazole-3-carboxylic acid ethyl ester

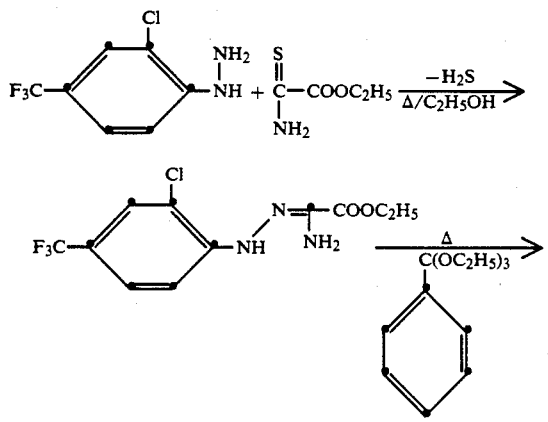

-continued

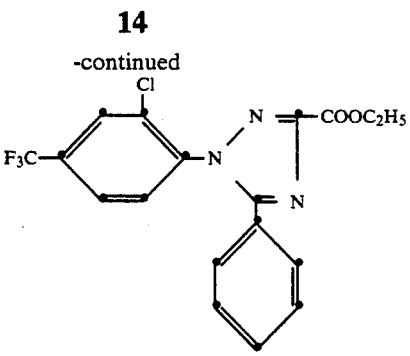

A mixture of 13.3 g (0.1 mol) of thiooxamide acid ethyl ester and 21.0 g (0.1 mol) of 2-chloro-4-trifluoromethyl-phenylhydrazine is refluxed in 400 ml of absolute ethanol for two hours. The hydrogen sulfide which is split off during this operation is passed through sodium hypochlorite solution for neutralisation. The clear, red reaction solution is concentrated by evaporation and the residue is purified with toluene over a short column of silica gel. Concentration of the main fraction of the eluate by evaporation yields 21.3 g (68.8% of the theoretical yield) of N-(2-chloro-4-trifluoromethyl-phenyl)-N'-amino-N'-ethoxycarbonylhydrazone having a melting point of 97°–98° C. which is heated together with 15.6 ml (0.069 mol) of orthobenzoic acid triethyl ester. At a bath temperature of 125° C. ethanol begins to distill off. When, by thin-layer chromatography, the end of the reaction has been determined, the reaction mixture is cooled. The residue is triturated with hexane and the light-beige product which crystallises is filtered off, yielding 22.4 g (82.7% of the theoretical yield) of 1-(2-chloro-4-trifluoromethylphenyl)-5-phenyl-1,2,4-triazole-3-carboxylic acid ethyl ester having a melting point of 107°–108° C.

EXAMPLE 2

Preparation of 1-(3-chlorophenyl)-5-(2-fluorophenyl)-1,2,4-triazole-3-carboxylic acid ethyl ester

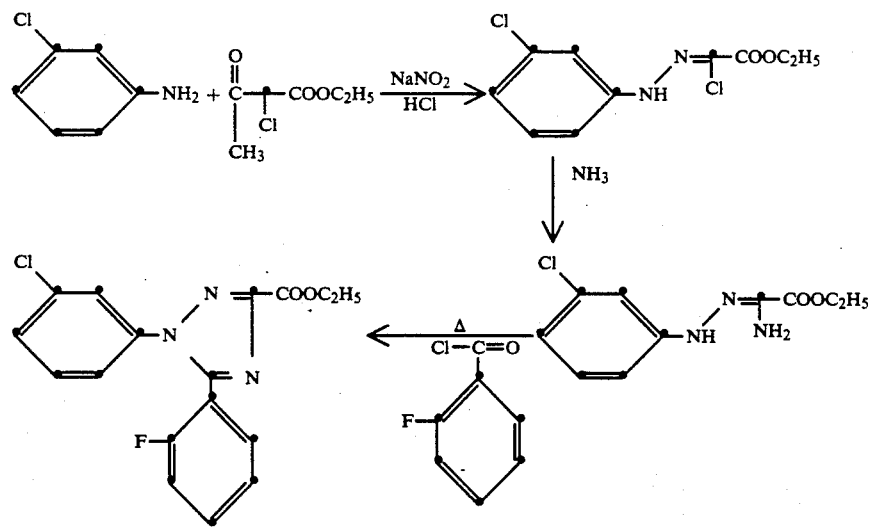

A solution of 14.0 g (0.202 mol) of sodium nitrite in 80 ml of water is added dropwise, at 0° C., to a suspension of 25.5 g (0.2 mol) of 3-chloroaniline in 80 ml of water and 65 ml of concentrated hydrochloric acid. After stirring for 15 minutes to complete the reaction, the foamy brown solution is poured into a mixture of 33.1 g (0.201 mol) of 2-chloroacetoacetic acid ethyl ester, 90 g of sodium acetate in 160 ml of water and 200 ml of ethanol. The whole is then stirred at 10° C. for 3 hours to complete the reaction. After the addition of 1 liter of water, a red oil separates and is extracted with ethyl acetate. After drying with magnesium sulfate and concentrating the extract there is obtained, in quantitative yield, an orange-red, crystalline material which is dissolved in 320 ml of tetrahydrofuran. 35 g (0.625 mol) of 25% aqueous ammonia are added dropwise at 15°-20° C. and the whole is then stirred for two hours. The end of the reaction is determined by thin-layer chromatography. 1 liter of water is then added and the resulting oil is extracted with ethyl acetate. After drying and concentrating the extract by evaporation, 40.7 g (84.4% of the theoretical yield) of an intermediate are obtained. 4.8 g (0.02 mol) thereof are dissolved in 30 ml of toluene, and 2.5 ml (0.021 mol) of 2-fluorobenzoyl chloride are added thereto. The clear, brown reaction solution is heated until water and hydrochloric acid separate out and the solvent has been distilled off. The residue is subjected to preliminary purification over a short column of silica gel and is then recrystallised from ether/hexane to yield 3.6 g (52.2% of the theoretical yield) of 1-(3-chlorophenyl)-5-(2-fluorophenyl)-1,2,4-triazole-3-carboxylic acid ethyl ester in the form of white-beige crystals melting at 77°-78° C.

EXAMPLE 3

Preparation of
1-(4-chlorophenyl)-5-phenyl-1,2,4-triazole-3-carboxylic acid methyl ester

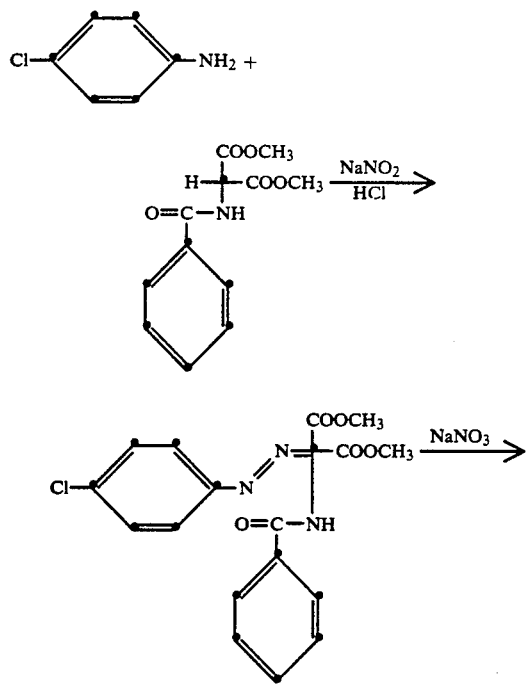

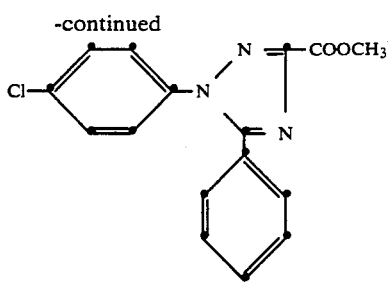

6.4 g (0.05 mol) of 4-chloroaniline are dissolved in a mixture of 50 ml of glacial acetic acid and 12.5 ml of concentrated hydrochloric acid, the solution is cooled to 0° C. and a solution of 3.5 g (0.0507 mol) of sodium nitrite in 6.5 ml of water is added dropwise. The reaction mixture is then cooled to −10° C. and a solution of 11.7 g (0.0466 mol) of benzoylaminomalonic acid dimethyl ester in 120 ml of acetone is added dropwise thereto. A solution of 70.2 g (0.509 mol) of potassium carbonate in 70 ml of water is then added dropwise and stirring is then carried out for a further half an hour at from 0° to 5° C. Ethyl acetate is then added to the reaction mixture. The organic phase is separated, washed with water, dried over sodium sulfate, filtered and concentrated by evaporation to produce, in quantitative yield, an intermediate in the form of a red clear oil. 9.75 g (0.025 mol) thereof are dissolved in 50 ml of methanol, and 0.7 g (0.004 mol) of 30% sodium methoxide in methanol is added. The reaction solution is left to stand overnight at room temperature during which the product crystallises out. After filtering off and washing with a small amount of methanol, 3.4 g (43.6% of the theoretical yield) of 1-(4-chlorophenyl)-5-phenyl-1,2,4-triazole-3-carboxylic acid methyl ester having a melting point of 136°-137° C. are obtained.

The following compounds are prepared analogously to these Examples:

TABLE 2

| No. | $(R_b)_n$ | $(R_a)_n$ | R | phys. data |
|---|---|---|---|---|
| 2.001 | 3-Cl | — | CH$_3$ | m.p. 127–129° |
| 2.002 | 2-Cl,4-CF$_3$ | — | C$_2$H$_5$ | m.p. 107–108° |
| 2.003 | — | — | C$_2$H$_5$ | m.p. 163–163° |
| 2.004 | 4-Cl | — | C$_2$H$_5$ | m.p. 130–131° |
| 2.005 | 2-Cl,4-Cl | — | C$_2$H$_5$ | m.p. 103–104° |
| 2.006 | 2-F,4-Cl, 5-OCH(CH$_3$)$_2$ | — | C$_2$H$_5$ | m.p. 131–132° |
| 2.007 | 3-Cl | 4-Cl | CH$_3$ | m.p. 113–114° |
| 2.008 | 3-CH$_3$ | 2-Cl | CH$_3$ | oil |
| 2.009 | 3-CH$_3$ | 2-F | CH$_3$ | m.p. 79–80° |
| 2.010 | 2-Cl | 2-Cl | CH$_3$ | m.p. 146–147° |
| 2.011 | 4-Cl | — | CH$_3$ | m.p. 136–137° |
| 2.012 | — | 2-Cl | C$_2$H$_5$ | m.p. 132–134° |
| 2.013 | 2-Cl | — | C$_2$H$_5$ | m.p. 121–122° |
| 2.014 | 2-NO$_2$ | — | C$_2$H$_5$ | m.p. 148–149° |
| 2.015 | 2-CH$_3$ | — | C$_2$H$_5$ | m.p. 114–115° |
| 2.016 | 3-Cl | 2-F | C$_2$H$_5$ | m.p. 77–78° |
| 2.017 | — | 2-F | C$_2$H$_5$ | m.p. 93–94° |

TABLE 2-continued

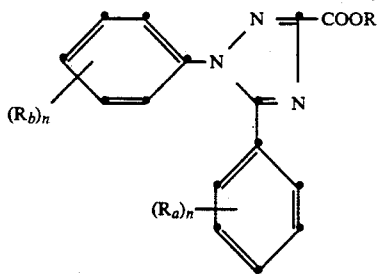

| No. | $(R_b)_n$ | $(R_a)_n$ | R | phys. data |
|---|---|---|---|---|
| 2.018 | — | 2-Cl | $C_2H_5$ | $n_D^{22}$ 1.5088 |
| 2.019 | 2-Cl,5-$CF_3$ | — | $C_2H_5$ | m.p. 157–158° |
| 2.020 | 2-$CH_3$,4-Cl | — | $C_2H_5$ | m.p. 109–110° |
| 2.021 | 2-F,5-$CF_3$ | — | $C_2H_5$ | m.p. 151–152° |
| 2.022 | 2-Cl | — | $CH_3$ | m.p. 104–106° |
| 2.023 | — | — | $CH_3$ | m.p. 160–162° |
| 2.024 | 2-Cl,4-$CF_3$ | — | $CH_3$ | |
| 2.025 | 2-Cl,4-$CF_3$ | — | $C_3H_7$-n | |
| 2.026 | 2-Cl,4-$CF_3$ | — | $CH_2CH=CH_2$ | |
| 2.027 | 2-Cl,4-$CF_3$ | — | $CH_2C\equiv CH$ | |
| 2.028 | 2-Cl | 2-Cl | $C_2H_5$ | |
| 2.029 | 2-Cl | 2-Cl | $CH(CH_3)_2$ | |
| 2.030 | 2-Cl | 2-Cl | $C_4H_9$-n | |
| 2.031 | 2-Cl | 2-Cl | $CH_2C\equiv CH$ | |
| 2.032 | 3-Cl | 2-F | $CH_3$ | |
| 2.033 | 3-Cl | 2-F | $C_5H_{11}$-n | |
| 2.034 | 2-Cl | 2-F | $CH_3$ | m.p. 84–87° |
| 2.035 | — | 2-F | $C_3H_7$-n | |
| 2.036 | — | 2-F | $CH_2CH=CH_2$ | |
| 2.037 | — | 2-F | $CH_2COOCH_3$ | |
| 2.038 | — | 2-F | $C_2H_4OCH_3$ | |
| 2.039 | — | 2-Cl | $CH_3$ | |
| 2.040 | — | 2-Cl | $C_3H_7$-n | |
| 2.041 | — | 2-Cl | Benzyl | |
| 2.042 | — | 2-Cl | 4-Methoxyphenyl | |
| 2.043 | 2-Cl | — | $C_4H_9$-n | |
| 2.044 | 2-Cl | — | $C_2H_4N(C_2H_5)_2$ | |
| 2.045 | 2-Cl | — | $C_3H_6Cl$ | |
| 2.046 | 2-Cl | — | $C_2H_4SCH_3$ | |
| 2.047 | 2-Cl | — | $CH_2COOC_2H_5$ | |
| 2.048 | 2-Cl | — | 2-Chlorobenzyl | |
| 2.049 | 2-$CH_3$ | — | $CH_3$ | m.p. 138° |
| 2.050 | 3-$CH_3$ | — | $CH_3$ | m.p. 159° |
| 2.051 | 4-$CH_3$ | — | $CH_3$ | m.p. 152° |
| 2.052 | 4-Br | — | $CH_3$ | m.p. 168° |
| 2.053 | 4-$OCH_3$ | — | $CH_3$ | m.p. 153° |
| 2.054 | — | — | H | m.p. 177–178° |
| 2.055 | — | — | $CH_3$ | m.p. 158–159° |
| 2.056 | 2-$CH_3$ | — | H | m.p. 171–172° |
| 2.057 | 3-$CH_3$ | — | H | m.p. 183–184° |
| 2.058 | 4-$CH_3$ | — | H | m.p. 177–178° |
| 2.059 | — | 2-F | $CH_3$ | |
| 2.059 | 4-$OCH_3$ | — | H | m.p. 176–177° |
| 2.060 | 4-Br | — | H | m.p. 179–180° |
| 2.061 | — | 4-Br | $CH_3$ | m.p. 157–159° |
| 2.062 | — | — | $C_2H_5$ | m.p. 176° |
| 2.063 | 3-$CH_3$ | — | $C_2H_5$ | |
| 2.064 | — | 4-$NO_2$ | $CH_3$ | m.p. 116–118° |
| 2.065 | 4-$NO_2$ | — | $CH_3$ | m.p. 179–181° |

The 1,5-diphenyl-1,2,4-triazole-3-carboxylic acids and derivatives of formula I according to the invention are used as safeners in admixture with herbicides, chloroacetanilides, N-benzoyl-N-phenyl-aniline derivatives or 2-[4-(phenoxy, pyridin-2-yloxy, 4-benzoxazol-2-yloxy, 4-benzothiazol-2-yloxy or 4-quinoxalin-2-yloxy)-phenoxy]propionic acid ester herbicides for controlling weeds in crops of useful plants.

The weeds to be controlled may be either monocotyledonous weeds or dicotyledonous weeds.

Suitable cultivated plants or parts of those plants are, for example, those mentioned above. Suitable areas of cultivation are areas of ground on which the cultivated plants are growing or that have been sown with the seeds of those cultivated plants and also ground that is intended for growing those cultivated plants.

Depending on the purpose of application, an antidote of formula I can be used for pretreating the seed of the cultivated plants (dressing of the seeds or cuttings) or can be applied to the soil before or after sowing. It may, however, also be applied on its own or together with the herbicide before or after the emergence of the plants. Treatment of the plant or the seed with the antidote may in principle, therefore, be carried out independently of the time of application of the phytotoxic chemical. Treatment of the plant may, however, be carried out also by simultaneous application of phytotoxic chemical and antidote (tank mix). Pre-emergence treatment includes both treatment of the cultivation area before sowing (ppi=pre plant incorporation) and treatment of the cultivation areas on which seeds have been sown but are not yet in growth.

The amount of the antidote to be applied in relation to the herbicide is largely dependent on the method of application. In the case of field treatment, which is carried out either using a tank mix comprising a combination of antidote and herbicide or by separate application of antidote and herbicide, the ratio of antidote to herbicide is normally from 1:100 to 10:1, preferably from 1:20 to 1:1 and especially 1:1. In the case of seed dressing, on the other hand, far smaller quantities of antidote are required in relation to the amount of herbicide used per hectare of cultivation area.

In the case of field treatment, from 0.001 to 1.0 kg of antidote/ha, preferably from 0.01 to 0.1 kg of antidote/ha, is normally applied.

In the case of seed dressing, from 0.01 to 10 g of antidote/kg of seed, preferably from 0.05 to 2 g of antidote/kg of seed, are generally applied. If the antidote is applied in liquid form shortly before sowing, resulting in swelling of the seed, antidote solutions that contain the active ingredient in a concentration of from 1 to 10,000, preferably from 100 to 1,000 ppm, are advantageously used. For application, the compounds of formula I or combinations of compounds of formula I with the herbicides to be rendered safe are advantageously used together with the adjuvants customary in the art of formulation and are therefore formulated in known manner e.g. into emulsifiable concentrates, coatable pastes, directly sprayable or dilutable solutions, dilute emulsions, wettable powders, soluble powders, dusts, granulates, and also encapsulation in e.g. polymer substances. As with the nature of the compositions, the methods of application, such as spraying, atomising, dusting, scattering, coating or pouring, are chosen in accordance with the intended objectives and the prevailing circumstances.

The formulations, i.e. the compositions, preparations or mixtures containing a compound (active ingredient) of formula I or a combination thereof with the herbicide that is to be rendered safe and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated and, where applicable, also on the nature of the herbicide that is to be rendered safe, suitable surface-active compounds are non-ionic, cationic and/or anionic surfactants having good emulsifying, dispersing and wetting properties. The term "surfactants" will also be understood as including mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Other suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical, alkyl also including the alkyl moiety of acyl radicals, for example the sodium or calcium salt of lignosulfonic acid, of dodecylsulfate or of a mixture of fatty alcohol sulfates obtained from natural fatty acids. These compounds also comprise the salts of the sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide; or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described inter alia in the following publications:

"McCutcheon's Detergents and Emulsifiers Annual", MC Publishing Corp., Ridgewood, New Jersey, 1981. Stache, H., "Tensid-Taschenbuch", Carl Hanser Verlag, Munich/Vienna, 1981.

The agrochemical compositions usually contain from 0.1 to 99% by weight, especially from 0.1 to 95% by weight, of a compound of formula I or an active ingredient mixture of antidote/herbicide, from 1 to 99.9% by weight, especially from 5 to 99.8% by weight, of a solid or liquid adjuvant, and from 0 to 25% by weight, especially from 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers and also fertilisers or other active ingredients for obtaining special effects.

For the use of compounds of formula I or compositions containing them for the protection of cultivated plants against the damaging effects of herbicides of formula II, various methods and techniques are suitable, such as, for example, the following:

i) Seed dressing a) dressing the seeds with an active ingredient of formula I formulated as a wettable powder by shaking in a vessel until evenly distributed over the surface of the seeds (dry dressing). In this case, approximately from 1 to 500 g of active ingredient of formula I (4 g to 2 kg of wettable powder) are used per 100 kg of seed.

b) dressing the seeds with an emulsifiable concentrate of the active ingredient of formula I according to method a) (wet dressing).

c) dressing by immersing the seed in a liquor containing 50-3200 ppm active ingredient of formula I for from 1 to 72 hours and optionally drying the seed subsequently (immersion dressing).

Dressing of the seed or treatment of the sprouted seedling are naturally the preferred methods of application since the active ingredient treatment is aimed completely at the target crop. Normally, from 1 to 500 g of antidote, preferably from 5 to 250 g of antidote, per 100 kg of seed are used and, depending on the method, which also allows the addition of other active ingredients or micronutrients, the upper and lower concentration limits specified can be varied (repetition dressing).

ii) Application from a tank mix

A liquid formulation of a mixture of antidote and herbicide (ratio to each other from 10:1 to 1:100) is used, the application rate of herbicide being from 0.01 to 1.0 kg per hectare. Such a tank mix is applied before or after sowing.

iii) Application in the drill

The antidote, formulated as an emulsifiable concentrate, wettable powder or granulate, is introduced into the open, sown drill and, when the drill has been covered in the normal way, the herbicide is then applied in the pre-emergence method.

iv) Controlled release of active ingredient

The active ingredient of formula I, in solution, is adsorbed onto granulated mineral carriers or polymerised granulates (urea/formaldehyde) and allowed to dry. A coating may optionally be applied (coated granulates) which allows the active ingredient to be released in a metered amount over a specific period.

| 1. Emulsifiable concentrates | a) | b) | c) |
|---|---|---|---|
| a compound of Table 2 or a mixture with a herbicide | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| a compound of Table 2 or a mixture with a herbicide | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 3. Granulates | a) | b) |
|---|---|---|
| a compound of Table 2 or a mixture with a herbicide | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | a) | b) |
|---|---|---|
| a compound of Table 2 or a mixture with a herbicide | 2% | 5% |
| highly dispersed silicic acid | 1% | 5% |
| talcum | 97% | — |
| kaolin | — | 90% |

Ready-for-use dusts are obtained by intimately mixing the active ingredient with the carriers.

| 5. Wettable powders | a) | b) | c) |
|---|---|---|---|
| a compound of Table 2 or a mixture with a herbicide | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrates | |
|---|---|
| a compound of Table 2 or a mixture with a herbicide | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any desired concentration can be produced from such concentrates by dilution with water.

| 7. Dusts | a) | b) |
|---|---|---|
| a compound of Table 2 or a mixture with a herbicide | 5% | 8% |
| talcum | 95% | — |
| kaolin | — | 92% |

Ready-for-use dusts are obtained by mixing the active ingredient with the carriers and grinding the mixture in a suitable mill.

| 8. Extruder granulates | |
|---|---|
| a compound of Table 2 or a mixture with a herbicide | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated granulates | |
|---|---|
| a compound of Table 2 or a mixture with a herbicide | 3% |
| polyethylene glycol (mol wt. 200) | 3% |
| kaolin | 94% |

The finely ground active ingredient is uniformly applied, in a mixer, to the kaolin moistened with polyethylene glycol. Non-dusty coated granulates are obtained in this manner.

| 10. Suspension concentrates | |
|---|---|
| a compound of Table 2 or a mixture with a herbicide | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, affording a suspension concentrate from which suspensions of any desired concentration can be obtained by dilution with water.

BIOLOGICAL EXAMPLES

The ability of the compounds of formula I to protect cultivated plants from the phytotoxic action of strong herbicides will be apparent from the following Examples. In the description of the tests, the compounds of formula I are referred to as safeners or antidotes.

In order to determine the protective action of the safener, the damage to the plant is evaluated on a linear nine-point assessment scale in which 1 represents 100% damage and 9 represents no damage (plant grows as the untreated reference plant). The herbicide is applied at a rate of application at which the test plant is partially damaged. In order to evaluate the action of the safener, the damage to plants that have been treated with the herbicide alone and to plants that have been treated with the herbicide and the antidote is determined. The difference in the ratings found for the herbicide and for the herbicide +safener gives the protective action. It is expressed as a percentage.

Testing of the protective action against herbicides in cereals. The herbicide and the antidote are applied postemergence in the form of a tank mix.

Wheat seeds of the variety "Besso" and barley seeds of the variety "Cornel" are sown separately in plastics pots (upper diameter 7 cm) in sandy clayey loam soil, covered with soil and then watered. The test plants are cultivated in a greenhouse and treated with the test compounds at the 2- to 3-leaf stage.

The compound to be tested as safener is dissolved in water and sprayed onto the plant together with the herbicide in 550 liters of mixture/ha.

The condition of the plants is assessed two weeks after the application. Completely untreated controls are used as a reference for this (100% growth). The damaging action is evaluated in percent. The difference in the damage between those plants treated with herbicide alone and those treated with herbicide and antidote is expressed as % protective action.

The results are summarised below.

The herbicide used is 2-[4-(5-chloro-3-fluoropyridin-2-yloxy)-phenoxy]-propionic acid methyl ester, and the antidote is identified by the number given in Table 2.

| herbicide concentration | safener No. | concentration | crop | protective action |
|---|---|---|---|---|
| 0.5 kg/ha | 2.002 | 0.4 kg/ha | wheat | 50% |
| 0.5 kg/ha | 2.008 | 0.4 kg/ha | wheat | 50% |
| 0.5 kg/ha | 2.011 | 0.4 kg/ha | wheat | 38% |

The herbicide used is the 2R enantiomer of 2-[4-(5-chloro-3-fluoropyridin-2-yloxy)-phenoxy]-propionic acid propynyl ester,

| 0.4 kg/ha | 2.016 | 0.4 kg/ha | wheat | 50% |
|---|---|---|---|---|
| 0.4 kg/ha | 2.017 | 0.4 kg/ha | wheat | 63% |
| 0.4 kg/ha | 2.018 | 0.4 kg/ha | wheat | 50% |
| 0.4 kg/ha | 2.020 | 0.4 kg/ha | wheat | 13% |
| 0.4 kg/ha | 2.021 | 0.4 kg/ha | wheat | 37% |
| 0.4 kg/ha | 2.022 | 0.4 kg/ha | wheat | 50% |

In an extended test procedure in which the condition of the plants is assessed only after 3 weeks, the following results were obtained:

Crop: Summer wheat "Besso"
Herbicide: 2-[4-(5-chloro-3-fluoropyridin-2-yloxy)-phenoxy]-propionic acid methyl ester

| herbicide concentration | safener No. | concentration | protective action |
|---|---|---|---|
| 0.5 kg/ha | — | | 0% |
| 0.5 kg/ha | 2.002 | 0.5 kg/ha | 63% |
| 0.5 kg/ha | 2.002 | 0.25 kg/ha | 63% |
| 0.5 kg/ha | 2.002 | 0.125 kg/ha | 63% |
| 0.5 kg/ha | 2.002 | 0.062 kg/ha | 50% |
| 0.25 kg/ha | 2.002 | 0.25 kg/ha | 63% |
| 0.25 kg/ha | 2.002 | 0.125 kg/ha | 75% |
| 0.25 kg/ha | 2.002 | 0.062 kg/ha | 63% |
| 0.25 kg/ha | 2.002 | 0.031 kg/ha | 75% |
| 0.125 kg/ha | 2.002 | 0.125 kg/ha | 50% |
| 0.125 kg/ha | 2.002 | 0.062 kg/ha | 38% |
| 0.125 kg/ha | 2.002 | 0.031 kg/ha | 63% |
| 0.125 kg/ha | 2.002 | 0.016 kg/ha | 38% |
| 0.5 kg/ha | 2.010 | 0.25 kg/hs | 50% |
| 0.5 kg/ha | 2.010 | 0.125 kg/ha | 63% |
| 0.5 kg/ha | 2.010 | 0.062 kg/ha | 63% |
| 0.25 kg/ha | 2.010 | 0.25 kg/ha | 63% |
| 0.25 kg/ha | 2.010 | 0.125 kg/ha | 63% |
| 0.25 kg/ha | 2.010 | 0.062 kg/ha | 63% |
| 0.25 kg/ha | 2.010 | 0.031 kg/ha | 50% |
| 0.125 kg/ha | 2.010 | 0.125 kg/ha | 38% |
| 0.125 kg/ha | 2.010 | 0.062 kg/ha | 50% |
| 0.125 kg/ha | 2.010 | 0.031 kg/ha | 50% |
| 0.125 kg/ha | 2.010 | 0.016 kg/ha | 50% |

Crop: Summer wheat "Besso"
Herbicide: 2-[4-(5-chloro-3-fluoropyridin-2-yloxy)-phenoxy]-propionic acid propynyl ester

| herbicide concentration | safener No. | concentration | protective action |
|---|---|---|---|
| 0.5 kg/ha | 2.002 | 0.5 kg/ha | 63% |
| 0.5 kg/ha | 2.002 | 0.25 kg/ha | 63% |
| 0.5 kg/ha | 2.002 | 0.125 kg/ha | 63% |
| 0.5 kg/ha | 2.002 | 0.062 kg/ha | 75% |
| 0.25 kg/ha | 2.002 | 0.25 kg/ha | 63% |
| 0.25 kg/ha | 2.002 | 0.125 kg/ha | 63% |
| 0.25 kg/ha | 2.002 | 0.062 kg/ha | 50% |
| 0.25 kg/ha | 2.002 | 0.031 kg/hs | 63% |
| 0.5 kg/ha | 2.010 | 0.25 kg/ha | 25% |
| 0.5 kg/ha | 2.010 | 0.125 kg/ha | 38% |
| 0.5 kg/ha | 2.010 | 0.062 kg/ha | 13% |

-continued

Crop: Summer wheat "Besso"
Herbicide: 2-[4-(5-chloro-3-fluoropyridin-2-yloxy)-phenoxy]-propionic acid propynyl ester

| herbicide concentration | safener No. | concentration | protective action |
| --- | --- | --- | --- |
| 0.25 kg/ha | 2.010 | 0.25 kg/ha | 63% |
| 0.25 kg/ha | 2.010 | 0.125 kg/ha | 75% |
| 0.25 kg/ha | 2.010 | 0.062 kg/ha | 75% |
| 0.25 kg/ha | 2.010 | 0.031 kg/ha | 75% |
| 0.125 kg/ha | 2.010 | 0.125 kg/ha | 25% |
| 0.125 kg/ha | 2.010 | 0.062 kg/ha | 25% |
| 0.125 kg/ha | 2.010 | 0.031 kg/ha | 38% |
| 0.125 kg/ha | 2.010 | 0.016 kg/ha | 38% |

Crop: Summer barley "Cornel"
Herbicide: 2-[4-(5-chloro-3-fluoropyridin-2-yloxy)-phenoxy]-propionic acid methyl ester

| herbicide concentration | safener No. | concentration | protective action |
| --- | --- | --- | --- |
| 0.25 kg/ha | 2.002 | 0.25 kg/ha | 50% |
| 0.25 kg/ha | 2.002 | 0.125 kg/ha | 38% |
| 0.25 kg/ha | 2.002 | 0.062 kg/ha | 25% |
| 0.25 kg/ha | 2.002 | 0.031 kg/ha | 38% |
| 0.125 kg/ha | 2.002 | 0.125 kg/ha | 38% |
| 0.125 kg/ha | 2.002 | 0.062 kg/hs | 50% |
| 0.125 kg/ha | 2.002 | 0.031 kg/ha | 50% |
| 0.125 kg/ha | 2.002 | 0.016 kg/ha | 38% |

Crop: Summer barley "Cornel"
Herbicide: 2-[4-(5-chloro-3-fluoropyridin-2-yloxy)-phenoxy]-propionic acid propynyl ester

| herbicide concentration | safener No. | concentration | protective action |
| --- | --- | --- | --- |
| 0.5 kg/ha | 2.002 | 0.5 kg/ha | 38% |
| 0.5 kg/ha | 2.002 | 0.25 kg/ha | 38% |
| 0.5 kg/ha | 2.002 | 0.125 kg/ha | 50% |
| 0.5 kg/ha | 2.002 | 0.062 kg/ha | 63% |
| 0.25 kg/ha | 2.002 | 0.25 kg/ha | 75% |
| 0.25 kg/ha | 2.002 | 0.125 kg/ha | 75% |
| 0.25 kg/ha | 2.002 | 0.062 kg/ha | 63% |
| 0.25 kg/ha | 2.002 | 0.031 kg/ha | 75% |
| 0.125 kg/ha | 2.002 | 0.125 kg/ha | 50% |
| 0.125 kg/ha | 2.002 | 0.062 kg/ha | 50% |
| 0.125 kg/ha | 2.002 | 0.031 kg/ha | 50% |
| 0.125 kg/ha | 2.002 | 0.016 kg/ha | 50% |
| 0.125 kg/ha | 2.010 | 0.125 kg/ha | 38% |
| 0.125 kg/ha | 2.010 | 0.062 kg/ha | 38% |
| 0.125 kg/ha | 2.010 | 0.031 kg/ha | 13% |
| 0.125 kg/ha | 2.010 | 0.016 kg/ha | 13% |

Crop: Summer barley "Cornel"
Herbicide: N-benzoyl-N-(3-chloro-4-fluorophenyl)-alanine methyl ester

| herbicide concentration | safener No. | concentration | protective action |
| --- | --- | --- | --- |
| 1 kg/ha | 2.002 | 0.2 kg/ha | 55% |
| 1 kg/ha | 2.002 | 0.1 kg/ha | 60% |
| 0.5 kg/ha | 2.002 | 0.2 kg/ha | 30% |
| 0.5 kg/ha | 2.002 | 0.1 kg/ha | 35% |
| 1 kg/ha | 2.022 | 0.2 kg/ha | 35% |
| 1 kg/ha | 2.022 | 0.1 kg/ha | 35% |
| 0.5 kg/ha | 2.022 | 0.2 kg/ha | 15% |
| 0.5 kg/ha | 2.022 | 0.1 kg/ha | 20% |
| 1 kg/ha | 2.034 | 0.2 kg/ha | 40% |
| 1 kg/ha | 2.034 | 0.1 kg/ha | 50% |
| 0.5 kg/ha | 2.034 | 0.2 kg/ha | 30% |
| 0.5 kg/ha | 2.034 | 0.1 kg/ha | 25% |

Crop: Summer wheat "Besso"
Herbicide: The 2R enantiomer of 2-[4-(5-chloro-3-fluoro-pyridin-2-yloxy)-phenoxy]-propionic acid propynyl ester

| herbicide concentration | safener No. | concentration | protective action |
| --- | --- | --- | --- |
| 400 g/ha | 2.016 | 400 g/ha | 75% |
| 400 g/ha | 2.016 | 200 g/ha | 63% |
| 400 g/ha | 2.016 | 100 g/ha | 50% |
| 400 g/ha | 2.016 | 50 g/ha | 38% |
| 200 g/ha | 2.016 | 200 g/ha | 63% |
| 200 g/ha | 2.016 | 100 g/ha | 63% |
| 200 g/ha | 2.016 | 50 g/ha | 63% |
| 200 g/ha | 2.016 | 25 g/ha | 38% |
| 100 g/ha | 2.016 | 100 g/ha | 38% |
| 100 g/ha | 2.016 | 50 g/ha | 38% |
| 100 g/ha | 2.016 | 25 g/ha | 38% |
| 100 g/ha | 2.016 | 13 g/ha | 38% |
| 400 g/hs | 2.017 | 400 g/ha | 63% |
| 400 g/hs | 2.017 | 200 g/ha | 75% |
| 400 g/ha | 2.017 | 100 g/ha | 50% |
| 400 g/ha | 2.017 | 50 g/ha | 38% |
| 200 g/ha | 2.017 | 200 g/ha | 63% |
| 200 g/ha | 2.017 | 100 g/ha | 75% |
| 200 g/ha | 2.017 | 50 g/ha | 63% |
| 200 g/ha | 2.017 | 25 g/ha | 50% |
| 100 g/ha | 2.017 | 100 g/ha | 50% |
| 100 g/ha | 2.017 | 50 g/ha | 50% |
| 100 g/ha | 2.017 | 25 g/hs | 50% |
| 100 g/ha | 2.017 | 13 g/ha | 38% |

Crop: Summer wheat "Besso"
Herbicide: The 2R enantiomer of 2-[4-(5-chloro-3-fluoro-pyridin-2-yloxy)-phenoxy]-propionic acid propynyl ester

| herbicide concentration | safener No. | concentration | protective action |
| --- | --- | --- | --- |
| 400 g/ha | 2.018 | 400 g/ha | 75% |
| 400 g/ha | 2.018 | 200 g/ha | 75% |
| 400 g/ha | 2.018 | 100 g/ha | 63% |
| 400 g/ha | 2.018 | 50 g/ha | 63% |
| 200 g/ha | 2.018 | 200 g/ha | 63% |
| 200 g/ha | 2.018 | 100 g/ha | 63% |
| 200 g/ha | 2.018 | 50 g/ha | 75% |
| 200 g/ha | 2.018 | 25 g/ha | 75% |
| 100 g/ha | 2.018 | 100 g/ha | 38% |
| 100 g/ha | 2.018 | 50 g/ha | 50% |
| 100 g/ha | 2.018 | 25 g/ha | 63% |
| 100 g/ha | 2.018 | 13 g/ha | 63% |
| 400 g/ha | 2.022 | 400 g/ha | 50% |
| 400 g/ha | 2.022 | 200 g/ha | 50% |
| 400 g/ha | 2.022 | 100 g/ha | 38% |
| 400 g/ha | 2.022 | 50 g/ha | 25% |
| 200 g/ha | 2.022 | 200 g/ha | 63% |
| 200 g/ha | 2.022 | 100 g/ha | 63% |
| 200 g/ha | 2.022 | 50 g/ha | 63% |
| 200 g/ha | 2.022 | 25 g/ha | 63% |
| 100 g/ha | 2.022 | 100 g/ha | 50% |
| 100 g/ha | 2.022 | 50 g/ha | 63% |
| 100 g/ha | 2.022 | 25 g/ha | 63% |
| 100 g/ha | 2.022 | 13 g/ha | 63% |

Crop: Summer wheat "Besso"
Herbicide: The 2R enantiomer of 2-[4-(5-chloro-3-fluoro-pyridin-2-yloxy)-phenoxy]-propionic acid propynyl ester

| herbicide concentration | safener No. | concentration | protective action |
| --- | --- | --- | --- |
| 200 g/ha | A | 200 g/ha | 25% |
| 200 g/ha | A | 100 g/ha | 25% |
| 200 g/ha | A | 25 g/ha | 25% |
| 100 g/ha | A | 100 g/ha | 38% |
| 100 g/ha | A | 50 g/ha | 25% |
| 100 g/ha | A | 25 g/ha | 38% |
| 100 g/ha | A | 13 g/ha | 38% |

Safener A is 1-(3-chlorophenyl)-5-trichloromethyl-1,2,4-triazole-3-carboxylic acid ethyl ester, known from DE-A 3 525 505.

Crop: Summer barley "Cornel"
Herbicide: The 2R enantiomer of 2-[4-(5-chloro-3-fluoro-pyridin-2-yloxy)-phenoxy]-propionic acid propynyl ester

| herbicide concentration | safener No. | concentration | protective action |
|---|---|---|---|
| 400 g/ha | 2.016 | 400 g/ha | 63% |
| 400 g/ha | 2.016 | 200 g/ha | 50% |
| 400 g/ha | 2.016 | 100 g/ha | 38% |
| 400 g/ha | 2.016 | 50 g/ha | 13% |
| 200 g/ha | 2.016 | 200 g/ha | 38% |
| 200 g/ha | 2.016 | 100 g/ha | 50% |
| 200 g/ha | 2.016 | 50 g/ha | 25% |
| 100 g/ha | 2.016 | 100 g/ha | 50% |
| 100 g/ha | 2.016 | 50 g/ha | 50% |
| 100 g/ha | 2.016 | 25 g/ha | 50% |
| 100 g/ha | 2.016 | 13 g/ha | 38% |
| 400 g/ha | 2.017 | 400 g/ha | 50% |
| 400 g/ha | 2.017 | 200 g/ha | 38% |
| 200 g/ha | 2.017 | 200 g/ha | 63% |
| 200 g/ha | 2.017 | 100 g/ha | 13% |
| 100 g/ha | 2.017 | 100 g/ha | 50% |
| 100 g/ha | 2.017 | 50 g/ha | 13% |

Crop: Summer barley "Cornel"
Herbicide: The 2R enantiomer of 2-[4-(5-chloro-3-fluoro-pyridin-2-yloxy)-phenoxy]-propionic acid propynyl ester

| herbicide concentration | safener No. | concentration | protective action |
|---|---|---|---|
| 400 g/ha | 0018 | 400 g/ha | 50% |
| 400 g/ha | 0018 | 200 g/ha | 25% |
| 200 g/ha | 0018 | 200 g/ha | 38% |
| 200 g/ha | 0018 | 100 g/ha | 13% |
| 100 g/ha | 0018 | 100 g/ha | 38% |
| 100 g/ha | 0018 | 50 g/ha | 13% |
| 100 g/ha | 0018 | 25 g/ha | 25% |

Crop: Summer barley "Cornel"
Herbicide: 2R-2-[4-(5-chloro-3-fluoropyridin-2-yloxy-phenoxy]-propionic acid propynyl ester

| herbicide concentration | safener No. | concentration | protective action |
|---|---|---|---|
| 400 g/ha | A | 400 g/ha | 0% |
| 400 g/ha | A | 200 g/ha | 13% |
| 400 g/ha | A | 100 g/ha | 0% |
| 400 g/ha | A | 50 g/ha | 0% |
| 200 g/ha | A | 200 g/ha | 0% |
| 200 g/ha | A | 100 g/ha | 13% |
| 200 g/ha | A | 50 g/ha | 0% |
| 200 g/ha | A | 25 g/ha | 0% |
| 100 g/ha | A | 100 g/ha | 25% |
| 100 g/ha | A | 50 g/ha | 13% |
| 100 g/ha | A | 25 g/ha | 25% |
| 100 g/ha | A | 13 g/ha | 25% |

Safener A is 1-(3-chlorophenyl)-5-trichloromethyl-1,2,4-triazole-3-carboxylic acid ethyl ester, known from DE-A 3 505 205.

2. Testing of the protective action against herbicides in sorghum.

2.1 The antidote is applied by seed dressing, and the herbicide is applied in the pre-emergence method.

Sorghum seeds are mixed in a glass vessel with the compound to be tested as antidote. Seeds and product are mixed together well by shaking and rotating. Pots of the same size (upper diameter 11 cm) are filled with soil and dressed seeds are sown therein. After covering the seeds, the herbicide is applied preemergence. The protective action of the antidote is assessed as a percentage 14 days after application of the herbicide. Completely untreated control plants are used as a reference for this. The results are as follows:

Crop: Sorghum of the variety Funk G-623
Herbicide: N-chloroacetyl-N-(2-methoxy-1-methylethyl)-2-ethyl-6-methylaniline

| herbicide cocentration | safener No. | concentration | protective action |
|---|---|---|---|
| 4 kg/ha | 2.002 | 2 g/kg | 50% |
| 4 kg/ha | 2.002 | 0.5 g/kg | 13% |
| 4 kg/ha | 2.002 | 0.125 g/kg | 13% |
| 4 kg/ha | 2.002 | 0.031 g/kg | 13% |
| 2 kg/ha | 2.002 | 2 g/kg | 63% |
| 2 kg/ha | 2.002 | 0.5 g/kg | 50% |
| 2 kg/ha | 2.002 | 0.125 g/kg | 25% |
| 2 kg/ha | 2.002 | 0.031 g/kg | 13% |
| 1 kg/ha | 2.002 | 2 g/kg | 63% |
| 1 kg/ha | 2.002 | 0.5 g/kg | 63% |
| 1 kg/ha | 2.002 | 0.125 g/kg | 50% |
| 1 kg/ha | 2.002 | 0.031 g/kg | 38% |

2.2 The herbicide and the antidote are applied pre-emergence in the form of a tank mix.

Sorghum seeds of the variety Funk G-623 are sown in sandy clayey loam soil in plastics pots (upper diameter 7 cm), covered with soil and then watered.

The compound to be tested as safener is dissolved in water and sprayed onto the soil pre-emergence together with the herbicide in 550 liters of mixture/ha.

The protective action of the safener is evaluated two weeks after the application. Completely untreated control plants are used as a reference for this (100% growth). The damaging action is evaluated as a percentage. The difference in damage caused to plants treated with herbicide alone and to those treated with herbicide and antidote is expressed as % protective action.

The results are summarised below.

The herbicide used for the sorghum is N-chloroacetyl-N-(2-methoxy-1-methylethyl)-2-ethyl-6-chloroaniline. The antidote is identified by the number given in Table 2.

| herbicide concentration | safener No. | concentration | protective action |
|---|---|---|---|
| 1.5 kg/ha | 2.002 | 1.5 kg/ha | 38% |
| 1.5 kg/ha | 2.016 | 1.5 kg/ha | 25% |
| 1.5 kg/ha | 2.020 | 1.5 kg/ha | 25% |
| 1.5 kg/ha | 2.022 | 1.5 kg/ha | 13% |

In an extended test procedure in which the condition of the plants was evaluated only after 3 weeks, the following results were obtained:

| herbicide concentration | safener No. | concentration | protective action |
|---|---|---|---|
| 4 kg/ha | 2.002 | 4 kg/ha | 25% |
| 4 kg/ha | 2.002 | 2 kg/ha | 13% |
| 4 kg/ha | 2.002 | 1 kg/ha | 13% |
| 2 kg/ha | 2.002 | 2 kg/hs | 13% |
| 2 kg/ha | 2.002 | 1 kg/hs | 13% |
| 1 kg/ha | 2.002 | 1 kg/ha | 38% |
| 1 kg/ha | 2.002 | 0.5 kg/ha | 25% |

We claim:
1. A selective herbicidal composition for controlling weeds and grasses in crops of useful plants, comprising an inert carrier, a herbicidally-effective amount of a herbicide selected from the group consisting of an N-benzoyl-N-phenylalanine derivative of Formula XII and a 2-[4-(5-chloro-3-fluoropyridin-2-yloxy)phenoxy]-propionic acid ester of Formula XI:

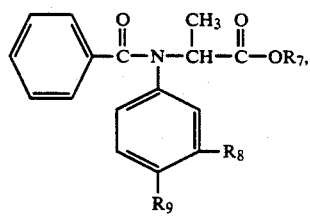
(XII)

wherein R₇ is hydrogen or $C_1$-$C_4$-alkyl and each of $R_8$ and $R_9$ is independently fluorine or chlorine;

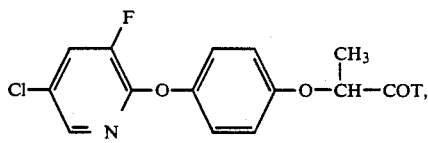
(XI)

wherein T is radical selected from the group consisting of methoxy, ethoxy, propoxy, isopropoxy, butoxy, dimethylaminoethoxy, propargyloxy, 1-cyano-1-methylethoxy, methoxycarbonylmethylthio, 1-ethoxycarbonylethoxy, acetooxim-oxy, methylethylketoxim-oxy and cyclohexanoxim-oxy; and a herbicide-antagonistically-effective amount of an antidote which is a 1,5-diphenyl-1,2,4-triazole-3-carboxylic acid derivative of formula I:

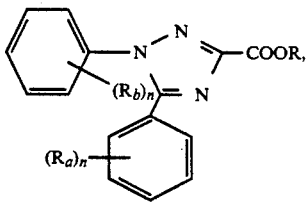
(I)

wherein each of $R_a$ and $R_b$, independently of the other, is halogen, $C_1$-$C_5$-alkyl, $C_1$-$C_5$-haloalkyl, $C_2$-$C_5$alkenyl, $C_2$-$C_5$-alkynyl, $C_1$-$C_5$-alkoxy, $C_1$-$C_5$-haloalkoxy, nitro or cyano, n is zero or a number from 1 to 3, R is hydrogen, a plant-physiologically tolerable metal or ammonium cation, or $C_1$-$C_8$-alkyl or $C_3$-$C_8$-cycloalkyl each of which is unsubstituted or mono- or poly-substituted by $C_1$-$C_4$-alkoxy, $C_1$-$C_4$-alkylthio, mono- or di-$C_1$-$C_4$-alkylamino, amino or $C_1$-$C_4$alkoxycarbonyl; $C_3$-$C_6$-alkenyl, unsubstituted or mono- or poly-substituted by halogen; $C_3$-$C_6$-alkynyl; phenyl or benzyl, which is unsubstituted or mono- or poly-substituted by halogen, nitro, $C_1$-$C_4$-alkyl, $C_1$-$C_4$-alkoxy, $C_1$-$C_4$-alkylthio, $C_1$-$C_4$-haloxlkyl, $C_1$-$C_4$-haloalkoxy or cyano.

2. A composition of claim 1, wherein the herbicide is of Formula XI wherein t is propargyloxy, or the 2R enantiomer thereof.

3. A composition of claim 1 wherein the herbicide is of Formula XI where T is propargyloxy, or the 2R enantiomer thereof, and wherein the antidote is of Formula I where n of $(R_a)_n$ is zero, n of $(R_b)_n$ is 1 and $(R_b)$ is 2-chloro, and R is methyl.

4. Composition according to claim 1, which contains as herbicidally active component N-chloroacetyl-N-(2-methoxy-1-methylethyl)-2-ethyl-6-methylaniline.

5. A composition according to claim 1, which contains as herbicidally active component N-benzoyl-N-(3,4-dichlorophenyl)-alanine-ethyl ester or N-benzoyl-N-(3-chloro-4-fluorophenyl)-alanine-methyl ester.

6. A method of protecting cultivated plants from the phytotoxic action of herbicides, which comprises treating the plants, the area in which they are grown or their seed, together with the herbicide or independently thereof with a herbicide antagonistic effective amount of a 1,5-di-phenyl-1,2,4-triazole-4-carbonic acid derivative according to claim 1.

* * * * *